United States Patent [19]

e Silva et al.

[11] Patent Number: 5,248,507
[45] Date of Patent: Sep. 28, 1993

[54] HYPERTONIC ISOCHLOREMIC FORMULATION FOR CIRCULATORY SHOCK

[75] Inventors: Mauricio R. e Silva; Irineu T. Velasco, both of Sao Paulo, Brazil; George C. Kramer, Galveston, Tex.

[73] Assignee: Board of Regents, The University of Texas System, Austin, Tex.

[21] Appl. No.: 708,029

[22] Filed: May 31, 1991

[51] Int. Cl.$^5$ .................. A61K 33/32; A61K 33/26; A61K 33/14; A61K 33/06; A61K 37/00; A61K 31/70; A61K 31/715; A61K 31/19

[52] U.S. Cl. .................. 424/643; 424/646; 424/680; 424/682; 514/2; 514/23; 514/59; 514/60; 514/557

[58] Field of Search .............. 424/600, 601, 680, 643, 424/646, 682; 514/561, 2, 23, 59, 60, 557

[56] References Cited

U.S. PATENT DOCUMENTS

| | | | |
|---|---|---|---|
| 3,993,750 | 11/1976 | Fox, Jr. | 424/128 |
| 4,049,795 | 9/1977 | Laborit | 424/180 |
| 4,908,350 | 3/1990 | Kramer et al. | 514/2 |
| 4,927,806 | 5/1990 | Kramer et al. | 514/2 |

OTHER PUBLICATIONS

Ekblad, H. et al., "Water, Sodium and Acid-Base Balance in Premature Infants: Therapeutical Aspects," Acta Paediatrica Scandinavica, 76(1):47–53, 1987.

Smith, G. J. et al., "A Comparison of Several Hypertonic Solutions for Resuscitation of Bled Sheep," Journal of Surgical Research, 39(6):517–528, 1985.

Excerpt from Advanced Trauma Life Support Instructor Manual, 1989.

Article by Kramer et al., "Small-volume Resuscitation With Hypertonic Saline Dextran Solution," Surgery, vol. 100, No. 2, pp. 239–246, Aug. 1986.

Abstract 21745 by Jan Modig, "Advantages of dextran 70 over Ringer acetate solution in shock treatment and in prevention of adult respiratory distress syndrome: A randomized study in man after traumatic-hemorrhagic shock," Resuscitation 10(4):219–226, 1983.

Article by John B. Cone et al., "Beneficial Effects of a Hypertonic Solution for Resuscitation in the Presence of Acute Hemorrhage," The Am. J. of Surgery, vol. 154, pp. 585–588, Dec. 1987.

Article by M. Rocha e Silva et al., "Hyperosmotic sodium salts reverse severe hemorrhagic shock: other solutes do not," The Am. Physiological Society, pp. H751–H762, 1987.

Abstract #122 by I. T. Velasco et al., "A Comparison of Hyperosmotic and Hyperoncotic Resuscitation from Severe Hemorrhagic Shock in Dogs," Circulatory Shock, vol. 21, No. 4, p. 338, 1987.

*Primary Examiner*—Frederick E. Waddell
*Assistant Examiner*—Raymond J. Henley, III
*Attorney, Agent, or Firm*—Arnold, White & Durkee

[57] ABSTRACT

The present invention relates to a hypertonic crystalloid resuscitation fluid particularly useful in treating circulatory shock arising from loss of blood. A pharmaceutical formulation prepared from sodium chloride in a range of about 2–7 osmolar parts and sodium acetate in a range of about 1–2 osmolar parts where the total osmolar concentration exceeds 500 mOsm can be used as a small volume rapid bolus resuscitation fluid which has little effect on plasma chloride levels. Blood flow is improved while arterial pressure is improved to the point of sustaining oxygen supply to tissues and organs in the recumbent recipient.

19 Claims, 12 Drawing Sheets

HYPERTONIC ISOCHLOREMIC FORMULATION FOR CIRCULATORY SHOCK

The United States Government may have certain rights to the usage of the present invention pursuant to the terms of Grant No. HL 40296 awarded by the National Institutes of Health.

BACKGROUND OF THE INVENTION

1. Field of the Invention

The invention relates generally to a fluid resuscitation composition useful for treatment of circulatory and ischemic shock. In particular, the composition is a hypertonic solution prepared from sodium acetate and sodium chloride which provides isochloremic resuscitation. Beneficial effects from administration are obtained rapidly, resulting in large increases in cardiac output and oxygen delivery to tissues. Consequences are increased arterial pressure minimally compatible with maintenance of adequate blood supply to body organs and tissues while minimizing increased blood loss associated with higher increases in arterial pressure.

2. Description of Related Art

Circulatory shock is a common life threatening pathophysiological state which occurs secondary to trauma, hemorrhage, burns, sepsis, allergic reactions and heart failure. These different types of circulatory shock are characterized by reduced blood pressure and cardiac output with a resultant reduction in blood flow and oxygen delivery to vital organs and tissues. This low blood flow condition causes local hypoxia, ischemia, and can lead to loss of cellular and organ function and even death. Accepted definitive treatment for some types of circulatory shock and useful therapy in all types of shock are volume infusions.

The standard of care in initial management of hemorrhagic shock is rapid administration of large volumes of isotonic crystalloid solution, several liters in an adult patient. The preferred fluid is Ringer's lactate, although normal saline or other similar isotonic crystalloid solutions are also used. Recommended continued treatment is based on the observed response to the initial fluid therapy (American College of Surgeons, 1988). As a general rule, guidelines are based on the "three for one" rule. This is based on the long-standing empirical observation that most hemorrhagic shock patients require up to 300 ml of electrolyte solution for each 100 ml of blood lost.

Other isotonic fluid replacement solutions have been used, including isotonic crystalloid solutions mixed with macromolecular solutions of plasma proteins or synthesized molecules with similar oncotic properties (colloids); including albumin, dextran, hetastarch or polygelatin in 0.9% NaCl. Whole blood is also used, but it is expensive, often unavailable and cross matching may delay therapy.

Crystalloids and colloids have been used as volume expanders, but generally must be infused in large volume. Such large volumes may cause peripheral and pulmonary edema. Additionally, the large volume requirements of isotonic fluids means that there are time delays and logistic difficulties associated with vascular delivery of effective therapy.

Hyperosmotic crystalloid and hyperosmotic/hyperoncotic (crystalloid/colloid) formulations offer some physiological benefits for the treatment of circulatory shock, including improved efficacy for restoration of overall cardiovascular function in animals and man compared to conventional resuscitation (Cone et al., 1987). Normalization of circulatory function has been obtained with such solutions (Kramer and Holcroft, 1990). Small volumes of salt/concentrated dextran formulations have been shown to rapidly restore and sustain normalization of circulatory function in hemorrhage (Kramer et al., 1986; Velasco et al., 1987). However, there remain some important limitations/side effects.

Hypertonic saline infusions in shocked animals and patients have been shown to cause an initial acidosis and hypokalemia. Treatment with hypertonic saline can also lead to a hyperchloremic acidosis, possibly due to excessive chloride load. Some isotonic Ringers solutions and mildly hypertonic formulations mimic sodium and chloride concentration ratios found in plasma and are thought to decrease the likelihood of acidosis (Fox, 1976). Circulatory shock is often associated with an acidosis and thus increased acidotic insult may be deleterious.

Although hypertonic saline rapidly improves both blood pressure and cardiac output, these beneficial effects may be overshadowed by deleterious effects from increased blood pressure. Uncontrolled internal bleeding in trauma patients may be aggravated by increased pressure, leading to increased bleeding. Return of normal blood pressure resulting in increased bleeding due to arterial pressure increase may lead to increased mortality over no treatment. Therefore, ideal pre-hospital resuscitation would increase cardiac output but only modestly increase blood pressure.

Another aspect of resuscitation fluids is their use under less than ideal (non hospital) conditions. Logistic restraints may severely curtail transportation of weighty or voluminous material. In battlefield situations it may be impractical to administer large volumes, yet there is a critical need to rapidly restore oxygen delivery to critical organs and to prevent or reverse the effects of traumatic shock.

SUMMARY OF THE INVENTION

The present invention is intended to address one or more of the problems associated with administration of currently used isotonic and hypertonic resuscitation fluids, particularly in the treatment of circulatory shock. The invention generally relates to a hypertonic crystalloid pharmaceutical composition that includes sodium acetate and sodium chloride. The particular composition is useful because it produces an isochloremic resuscitation. The composition is capable of restoring adequate blood flow to organs and tissues while maintaining arterial blood pressure at a level just sufficient to maintain blood flow to the recumbent mammal.

The Inventors have discovered that a pharmaceutical composition comprising sodium chloride and sodium acetate will unexpectedly maintain plasma chloride levels and prevent a hyperchloremic acidosis when administered as a resuscitation fluid. Isochloremic resuscitation is achieved only when sodium chloride and sodium acetate are present in certain relative concentrations, that is, about 2 to 7 osmolar parts sodium acetate and about 1-2 osmolar parts sodium chloride. In these relative osmolar concentration ranges, administration of the combined salt solution results in little, if any, change in the plasma chloride concentration. In a preferred embodiment, sodium chloride to sodium acetate ratio is approximately 2:6 osmolar parts in a solution with a total osmolarity of about 2400 mOsm parts. In a most preferred embodiment sodium chloride to sodium acetate ratio is approximately 1:7 osmolar parts with a total osmolarity of about 2400 mOsms.

As used herein, the term mOsm/L expresses milliosmoles per liter of solution. Osmolarity of a solution is a colligaive property determined by the pressure differential across a semipermeable membrane, e.g., a cell wall, engendered by a solvent and any dilute solution. The osmotic pressure of the dilute solution depends on the number of particles in solution, not on weight or type of solute. A mole of divalent salt thus provides 2 osmoles whereas a mole of sugar which is un-ionized provides 1 osmole. An osmole of solute in a liter of solution is a 1 osmolar solution An osmole of solute added to 1 kilogram of water is a 1 osmolal solution. Generally this slight difference in actual concentration is of little significance.

The new pharmaceutical composition typically induces a large increase in cardiac output with a modest rise in arterial blood pressure almost immediately upon administration. The rise is sufficient to maintain blood perfusion to essential body organs and to tissues while the transfusion recipient is in a recumbent position. Generally, the rise in arterial blood pressure will not be sufficient to maintain adequate blood profusion to body tissues if the subject is in an upright position. This finding was quite surprising because in general, increased blood flow after resuscitation will be accompanied by significant rise in arterial pressure. Such increases in arterial pressure are usually considered detrimental because of increased arterial bleeding which is particularly detrimental in cases of severe hypovolemia. Often the increased internal loss of blood is not compensated by administration of commonly used resuscitation fluids and fatal shock may ensue. Isotonic saline and hypertonic saline typically promote increased blood flow to body organs and tissues but the pressure rise is significantly higher than that observed with the pharmaceutical composition discovered by the inventors.

Typically, the pharmaceutical composition of the present invention will have a total osmolar concentration in excess of 500 mOsm. For general purposes, ideally these solutions will be around 2400 mOsm. The high osmolarity of the solution provides an effective fluid expander, thus fluid is pulled across cell membranes and the capillary wall. Water is redistributed through the interstitial and vascular spaces. High osmolarities result in rapid volume expansion, arteriolar vasodilation and increased contractility. Together, these changes cause an increase in cardiac output and oxygen delivery to tissues.

An unexpected aspect of the invention is an ability to provide increased blood flow to essential organs without causing an undue increase in arterial pressure. While 50:50 mixtures of sodium acetate:sodium chloride will enhance cardiac output and not unduly increase arterial pressures, such combinations are not isochloremic. Alternatively, pure hypertonic acetate mixtures cause hypochloremia and are not superior to hypertonic saline (Rocha e Silva et al., 1987). The new formulation is particularly valuable in preventing possible acidosis due to excess chloride ion precisely because it causes little alteration in plasma chloride levels. Several modifications of the pharmaceutical composition are possible, for example, a colloid or a crystalloid may be added to the preparation. Suitable colloids may include dextran soluble starches, gelatins and proteins, for example stroma-free hemoglobin. An example of the soluble starch is hydroxyethyl starch. Varying amounts of crystalloids could also be added, for example, magnesium salts, potassium salts and salts with appropriate anions having buffering capacity. However, it will be appreciated that while inclusion of colloids which have high molecular weights will have little effect on total osmolarity, low molecular weight species such as salts or amino acids may add significantly to total osmolarity. This is a consideration in preparing formulations for particular use. Additionally, other components may be added, for example, certain types of anti-shock drugs such as fructose diphosphate or ATP and $Mg^{++}$, as well as oxygen radical scavengers, neutrophil adherence inhibitors, leukotriene blockers, thromboxane blockers, calcium channel blockers and the like.

Yet another aspect of the invention is a method of providing intravascular support, generally to those patients suffering generally from circulatory shock caused by loss of blood, for example, or burn, sepsis, allergic reaction, heart failure or hemorrhage. The patient will be administered a bolus of an effective amount of a pharmaceutical composition having 1-2 osmolar parts of sodium chloride and 2-7 osmolar parts of sodium acetate with a total osmolarity of at least 500 mOsm/L. The amount will depend somewhat on the medical situation, the physiological state of the recipient and the total osmolarity of the solution employed. Administration is intravascular, preferably intravenous or intraosseus. The bolus is preferably administered rapidly, typically about 4-6 ml/kg over a period of 4-10 min.

Generally, fluid resuscitation is required under conditions of hypovolemia. Severe hypovolemia may result from a variety of insults, including surgeries such as orthopedic surgery. Massive blood loss may occur from surgeries necessary to repair or remove damaged liver, esophagus or other tissues and organs. The most common types of circulatory shock treated result from hemorrhaging or loss of blood through external or internal bleeding. Blood loss may be especially large in severe arterial bleeding, which may occur after a large artery or arteries are cut in lesions such as in trauma. Often in these cases, there is an initial blood loss which represents the dimension of the arterial lesion. Blood is lost at a variable rate which is proportional to the driving or arterial pressure. All types of circulatory shock are characterized by reduced blood pressure and cardiac output with the resultant reduction in blood flow and oxygen delivery to vital organs and tissue. Low flow causes local hypoxia, ischemia, possibly leading to loss of cellular and organ function and ultimately death.

The novel resuscitation fluid is a combination of sodium acetate and sodium chloride with a ratio of about 1-2 osmolar parts of sodium chloride and 2-7 osmolar parts of sodium acetate and a total osmolar concentration of at least 500 and preferably 2400 mOsm per liter. Although fluid replacement is possible through oral administration, the method is slow and relatively ineffective. Administration is preferably by intravenous infusion. The infusion should be administered quickly, typically over a period of between about 4 and 10 minutes.

Choice of the particular fluid composition and concentration used will depend on the situation in which it is used. A 2400 mOsm sodium chloride/sodium acetate (NaCl/NaAc) combined with a hyperoncotic colloid mixture may be ideal for prehospital resuscitation of shock and trauma. A single 250 ml 4 min bolus infusion would provide rapid improvement in cardiac output and oxygen delivery with only minimal increases in blood pressure and internal bleeding. Higher more concentrated sodium chloride/sodium acetate mixtures would be used when limited volumes of solution are available, for example in battlefield situations. At very high osmolar concentrations, relatively small amounts of fluid could be used for initial resuscitation. Volumes small enough to fit into a syringe may be readily transported in situations where weight and volume of medical supplies are a consideration. A typical situation might be emergency medical care by corpsmen in the battlefield for fluid resuscitation in severely wounded soldiers. In such cases, very small volumes of near saturated NaCl/NaAc solutions could be employed. In other environments, for example, intra-operative fluid supplementation, 1000 mOsm/L sodium chloride:-sodium acetate solutions are expected to effectively treat hypovolemia, maintain normal pH, increase cardiac output, but keep arterial blood pressure and surgical bleeding at lower levels than with other resuscitation regimens.

DETAILED DESCRIPTION OF THE PREFERRED EMBODIMENTS

The invention is a hypertonic crystalloid resuscitation fluid containing specified amounts of sodium chloride and sodium acetate. Surprisingly, the particular salt combination used as a pharmaceutical formulation has little effect on plasma chloride concentrations when administered to subjects in circulatory shock. This contrasts with most hypertonic salt solutions, whether sodium chloride alone or in various other combinations with sodium acetate. In addition to its isochloremic properties as a resuscitation fluid, the pharmaceutical composition discovered by the inventors provides a substantial increase in blood flow to tissues and organs while unexpectedly eliciting less of a rise in arterial pressure than other sodium-containing resuscitation solutions. The unexpected minimal arterial pressure rise is sufficient to maintain blood flow to critical organs while the subject is in a recumbent position but has the effect of minimizing internal bleeding in situations where such bleeding may be the cause of the shock. Additionally, the formulation increases oxygen consumption to an unexpected and superior degree compared to hypertonic saline formulations.

The novel pharmaceutical formulation is amenable to modification according to medical need; for example, in routine hospital procedures requiring fluid replacement or enhancement or in special situations, such as the need for immediate emergency medical care in isolated geographical areas. In critical situations, aggressive resuscitation with conventional resuscitation fluids frequently causes increased internal bleeding and hyperosmotic crystalloid solutions such as sodium chloride may also induce acidosis. Both these disadvantages are overcome by using the new isochloremic formulation.

The following examples illustrate preferred embodiments of the practice of the invention. It should be understood that these examples are intended to be illustrative of the invention and in no way limiting.

EXAMPLE 1

Effect of Chloride/Acetate Ratio on Plasma Electrolytes

Experiments were conducted to show the effect of hypertonic formulations of various ratios of sodium chloride and sodium acetate on plasma sodium ions and chloride.

Figure 1A:
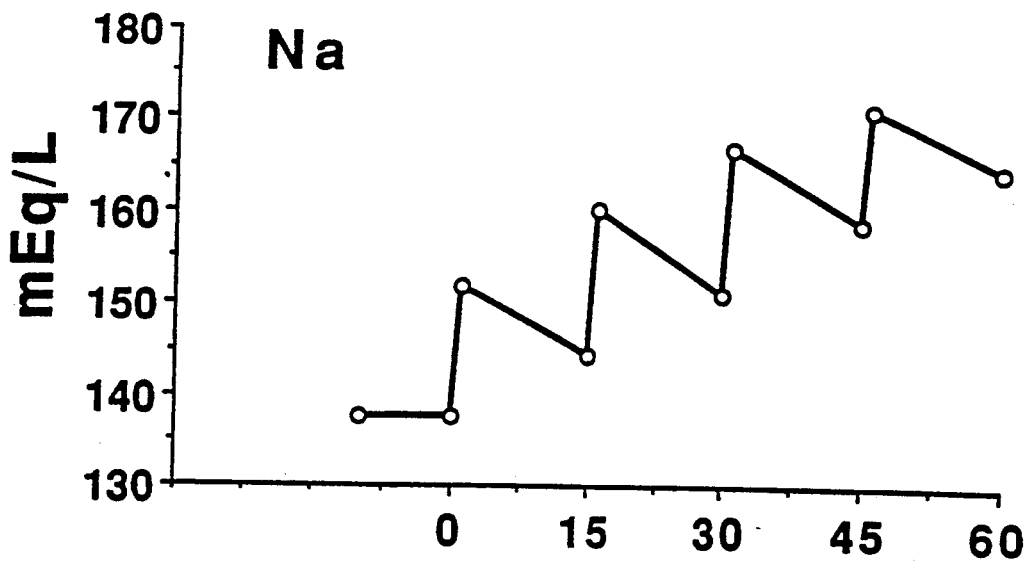
FIG. 1 shows the effect of infusion of various ratios of NaCl/NaAo into an anesthetized pig. Panel A shows the effect on plasma sodium ion levels. Panel B shows the effect on plasma chloride levels.
Figure 1B:
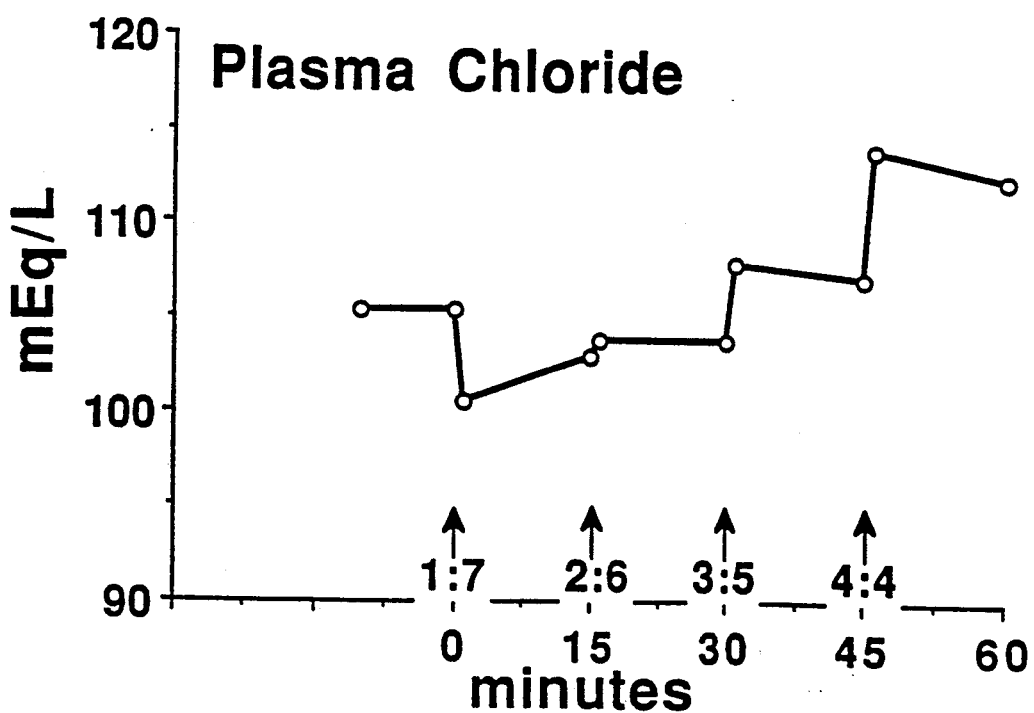
Figure 2:
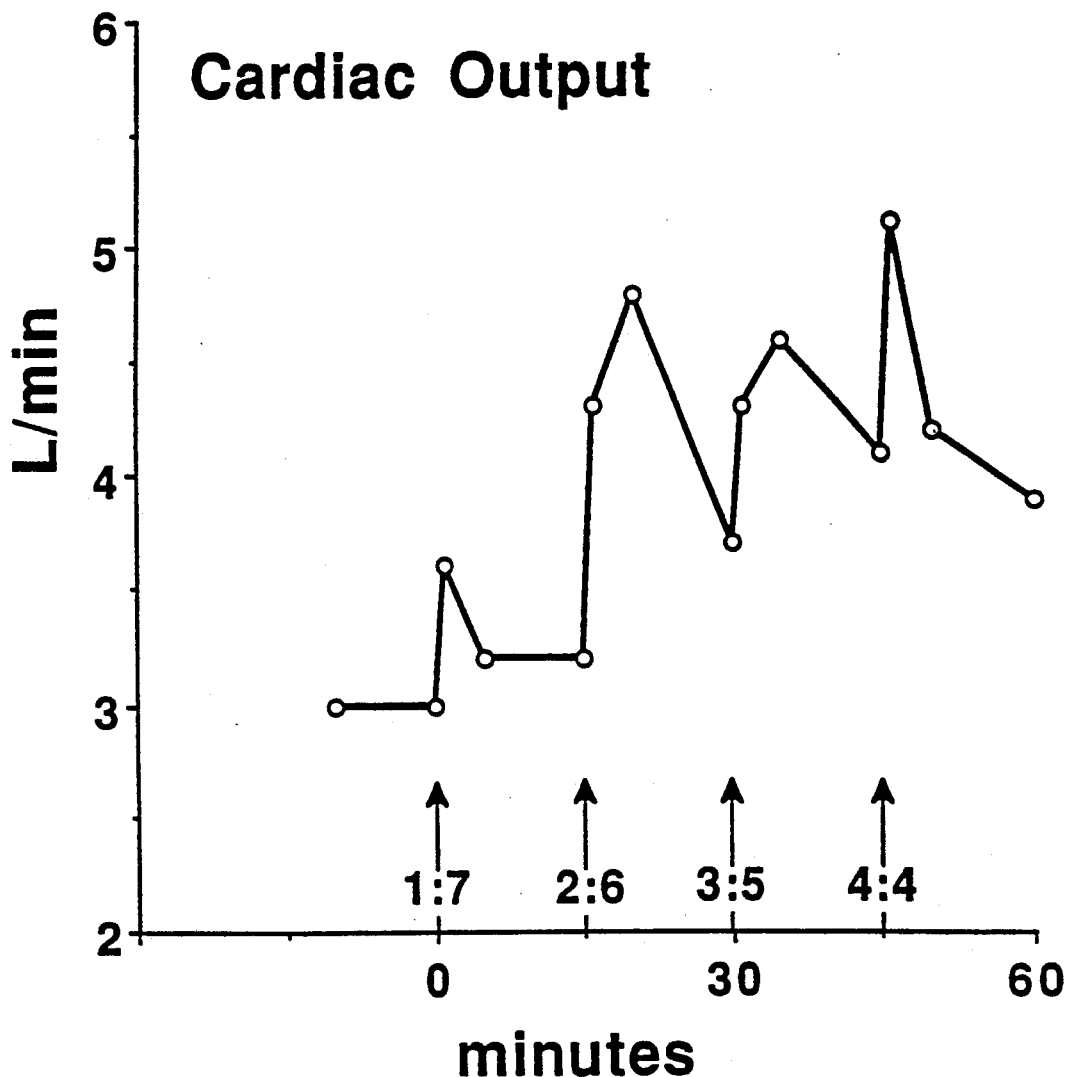
FIG. 2 shows the effect on cardiac output of infusing various ratios of hypertonic NaCl/NaAc solutions into a hemorrhaged pig.
Figure 3:
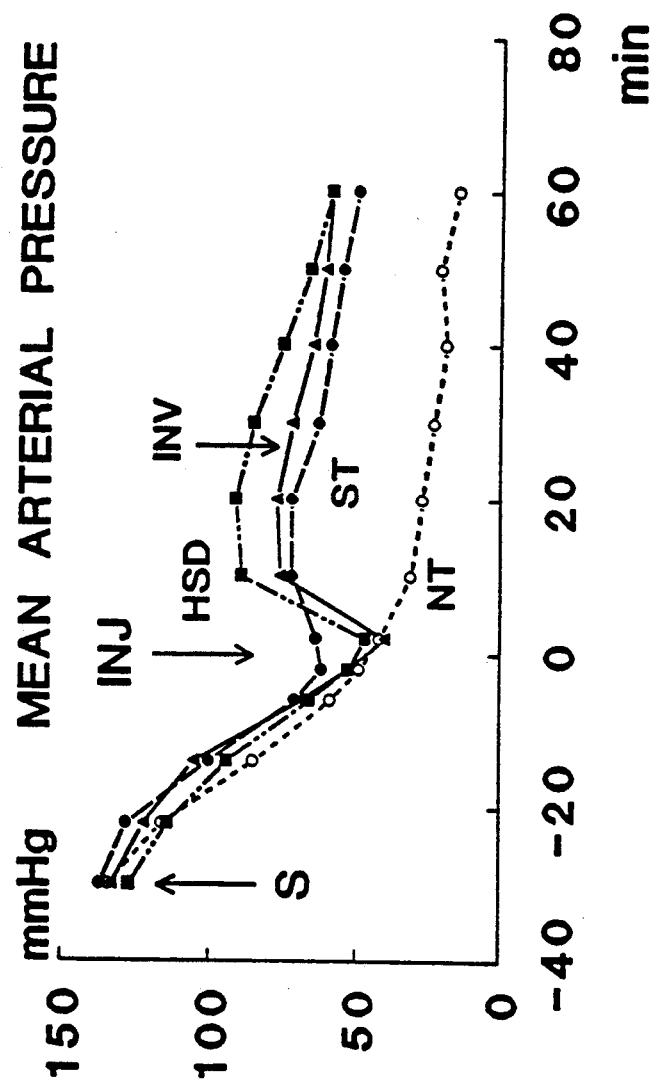
FIG. 3 shows the effects of unstopped hemorrhage (starting at S) and various treatments (starting at INJ) on arterial pressure of dogs.
Figure 4:
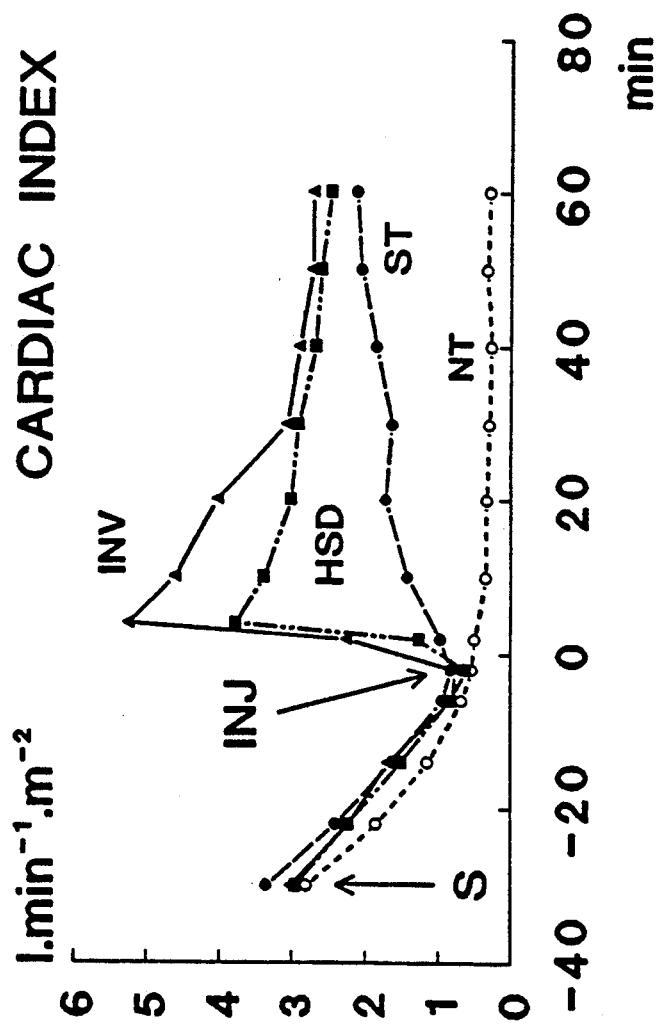
FIG. 4 shows effects of unstopped hemorrhage (starting at S) and treatments (starting at INJ) on cardiac output of dogs.

A pig was anesthetized with isoflurane. Vascular cannulas were placed in the aorta and vena cava and a thermodilution catheter placed in the pulmonary artery for hemodynamic monitoring. After a mild hemorrhage, the pig was infused with 4 ml/kg of 2400 mOsm of a 1:7 mixture of NaCl and NaAc. Blood samples were taken and hemodynamics measured. In subsequent 30 min periods, 4 ml/kg 2400 mOsm solutions of 2:6, 3:5 and 4:4 osmolar parts NaCl/NaAc were infused. FIG. 1A indicates plasma sodium ion levels after each infusion. FIG. 1B shows plasma chloride levels. Isochloremic resuscitation occurred with the 2:6 NaCl/NaAc mixture. FIG. 2 shows cardiac output after each infusion. Good augmentation of blood flow was shown with the 2:6 formulation.

EXAMPLE 2

Comparison of Hyperosmotic Chloride/Acetate with Standard Resuscitation Fluids in Managing Uncontrolled Bleeding The objective of the experiment was to determine the effect of using hyperosmotic sodium chloride:sodium acetate solutions on cardiovascular function in circumstances mimicking an average emergency rescue of patients undergoing intense blood loss.

Experiments were performed on dogs in controlled laboratory conditions designed to emulate the course of severe arterial bleeding as it may occur after a large artery or arteries are lesioned in trauma. In such a situation it is presumed that prehospital care, once it reaches the patient, is able to deliver resuscitative treatment but unable to interrupt the internal blood loss. The concept of arterial bleeding presumes (i) that there is an initial, predetermined rate of blood loss, which represents the dimension of the arterial lesion, and (ii) that blood will be lost at a variable rate which remains proportional to prevailing arterial pressure.

The initial bleeding rate was arbitrarily established at 25 ml/min, equivalent to a bleeding rate of 100 ml/min for a normal 70 kg human adult. Once started, bleeding was never interrupted, for a total duration of 90 min. Various alternative treatments were instituted at 30 min in different dogs.

In the first set of experiments, there were four groups of dogs: a $1^{st}$ group was left untreated (NT); a $2^{nd}$ group received the standard of care treatment consisting of a continuous infusion of 24 ml/min of crystalloid solution, from 30 to 90 min. (ST); a 3rd group received the same treatment as the ST group, but a rapid infusion of 6 ml/kg of hyperosmotic hyperoncotic NaCl (7.5%)+dextran70 (6%) was given at the beginning of treatment (HSD); a 4th group received the same as the ST group, but a rapid infusion of 6 ml/kg of the invention plus dextran was given at the beginning of resuscitation (INV). All groups were homogeneous in all respects before treatment.

Figure 5:
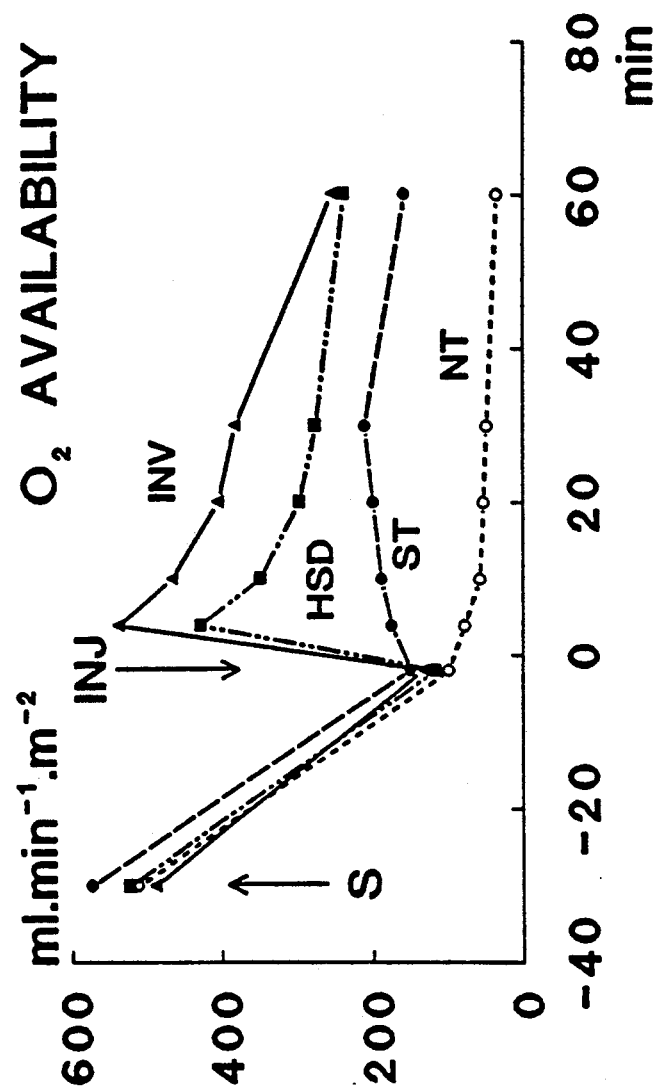
FIG. 5 shows effects of unstopped hemorrhage (starting at S) and treatments (starting at INJ) on $O_2$ availability of dogs.
Figure 6:
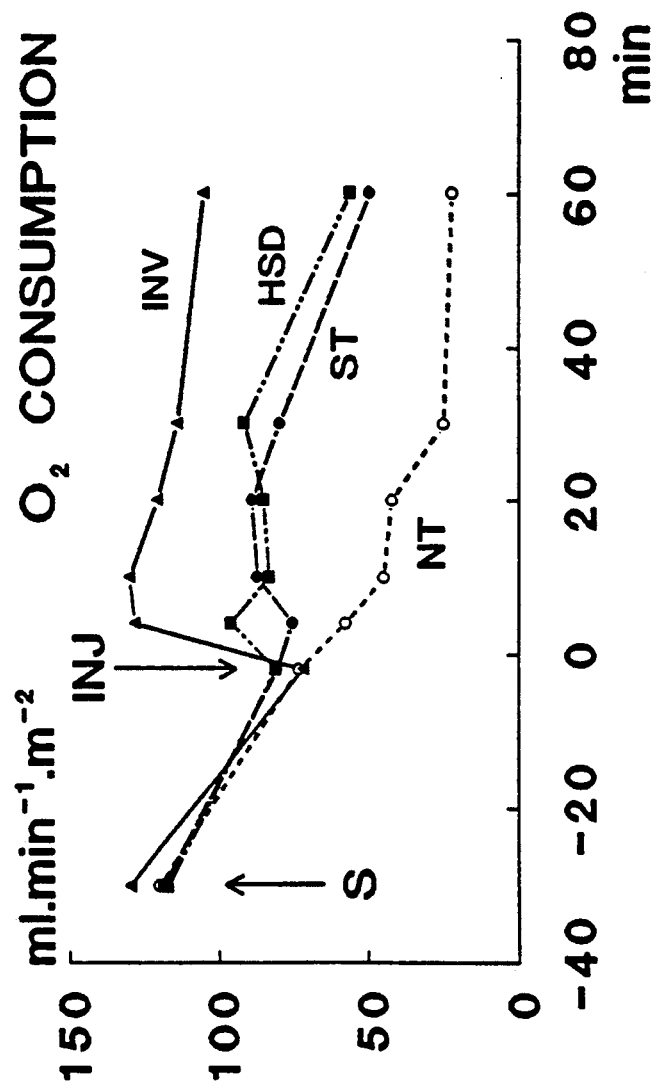
FIG. 6 shows effects of unstopped hemorrhage (starting at S) and treatments (starting at INJ) on $O_2$ consumption of dogs.
Figure 7:
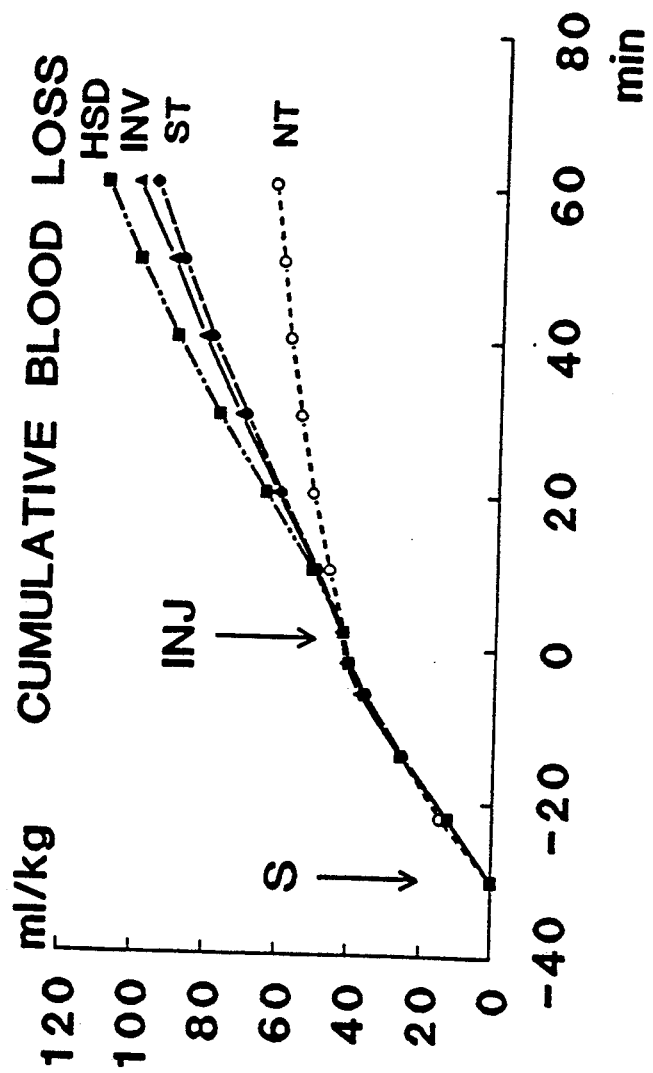
FIG. 7 shows effects of unstopped hemorrhage (starting at S) and treatments (starting at INJ) on blood pressure driven loss of dogs.

FIGS. 3–6 show that the NT group declines progressively to critically low levels of arterial pressure, cardiac output, oxygen availability, and oxygen consumption, even though the blood loss incurred is the smallest of all groups (FIG. 5). This smaller blood loss is a necessary consequence of the experimental concept. 90% of all dogs in this group died within the experimentation period. Deaths occurred between 40 and 90 min after the start of bleeding.

The ST group exhibited a gradual recovery of arterial pressure, cardiac output, oxygen availability and oxygen consumption, once the standard of care treatment was instituted.

The addition of HSD at the start of treatment (HSD group) elevated arterial pressure and cardiac output, in comparison to the ST group, but failed to clearly improve oxygen consumption, even though the oxygen availability was higher than that observed in the ST group.

Figure 8:
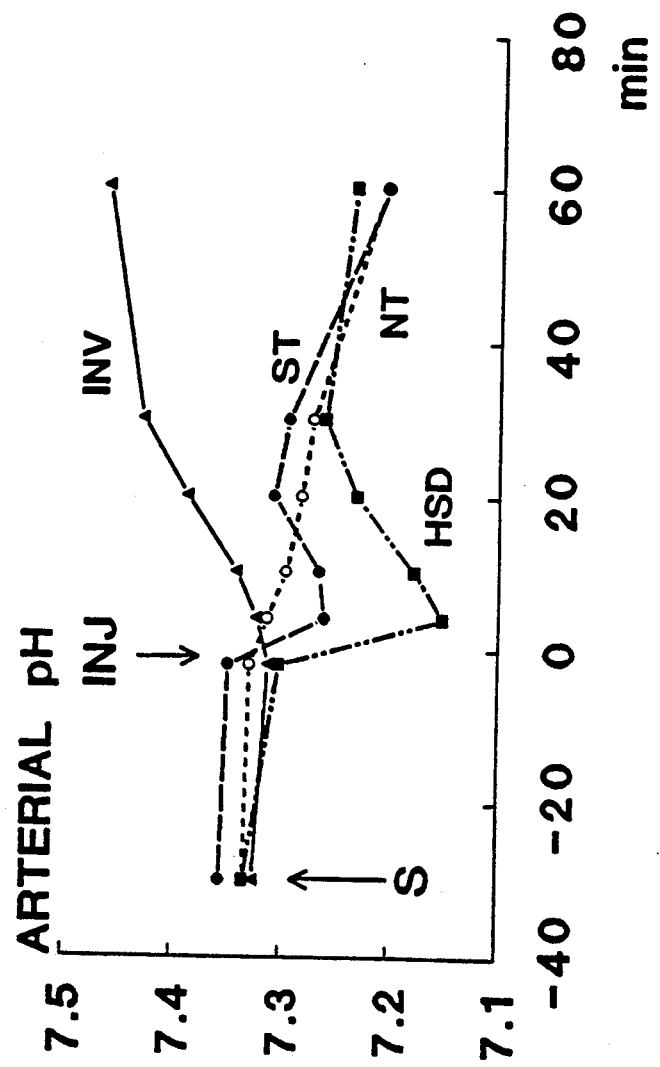
FIG. 8 shows effects of unstopped hemorrhage (starting at S) and treatments (starting at INJ) on arterial pH of dogs.
Figure 9:
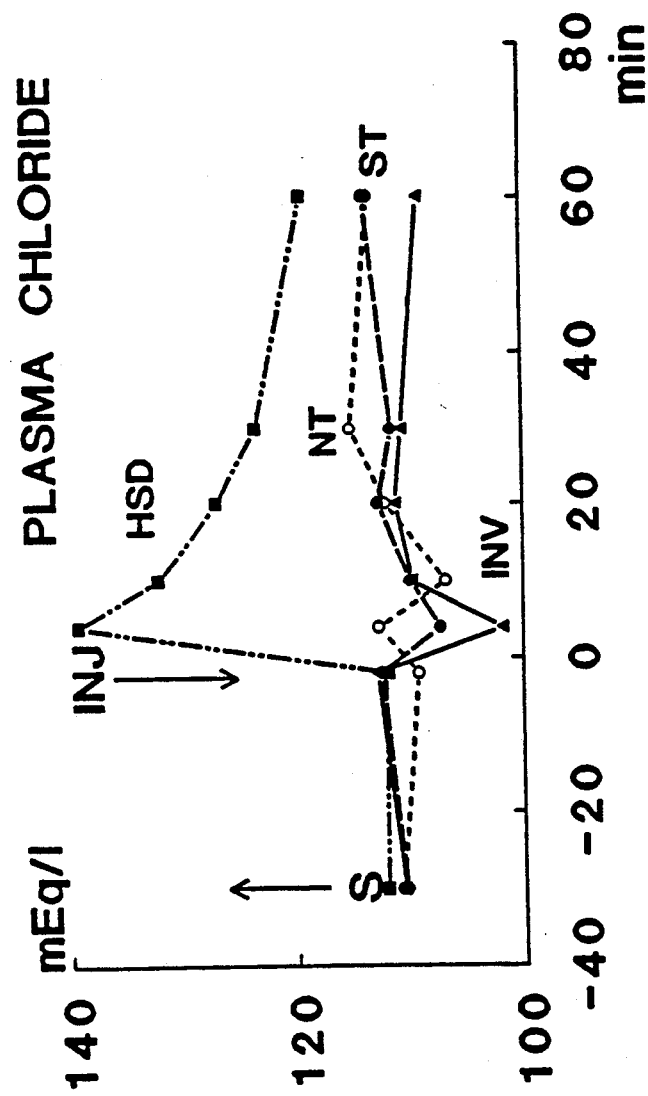
FIG. 9 shows effects of unstopped hemorrhage (starting at S) and treatments (starting at INJ) on plasma $Cl^-$ of dogs.

The addition of the INV fluid at the start of treatment did not significantly alter blood pressure by comparison with the ST group, but cardiac output, oxygen availability and oxygen consumption were much higher than observed in the other test groups. Unexpectedly, in the INV group, oxygen consumption recovered to essentially normal levels after approximately 30 minutes. FIGS. 8–9 show that while arterial pH drops in the HSD group, it remains stable in the INV group and that while the chloride level rises in the HSD group, it remains stable in the INV group.

EXAMPLE 3

Three groups of dogs were used as models for hypovolemia from severe arterial bleeding. Bleeding rates were established as in Example 2. One group of dogs received no treatment (NT); a second group received HSD alone, that is, a rapid infusion of 6 ml/kg of hyperosmotic/hyperoncotic NaCl (7.5%) plus dextran70 (6%) given at the beginning of treatment (HSD) and the last group received a hypertonic solution of 6 ml/kg of 2:6 osmolar parts of sodium chloride:sodium acetate, 2400 mOsm total INV alone.

Figure 10:
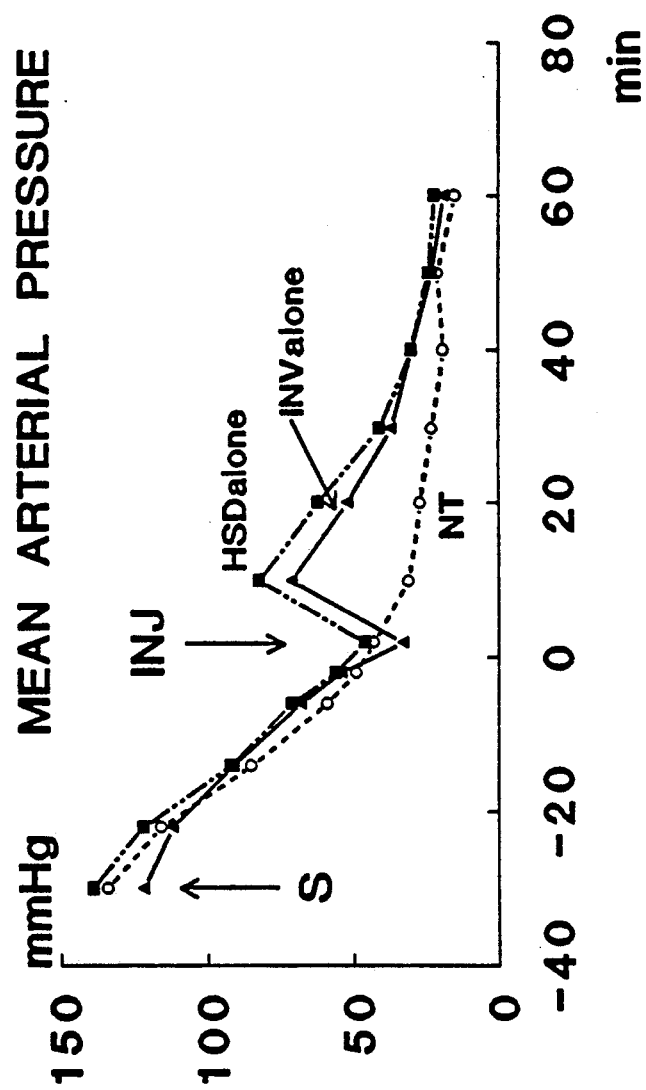
FIG. 10 shows the effect of NaCl/dextran (HSD) or NaCl/NaAc/dextran (INV) on arterial pressure of dogs with unstopped hemorrhage (starting at S). Time of administration is indicated at INJ.
Figure 11:
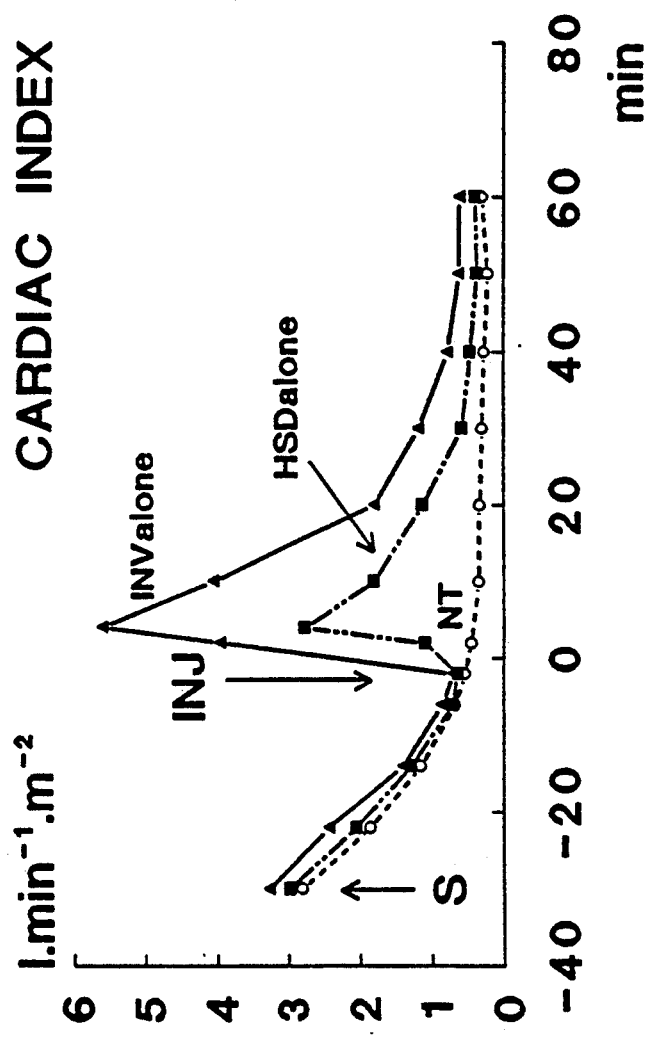
FIG. 11 shows the effect of NaCl/dextran (HSD) or NaCl/NaAc/dextran (INV) on cardiac index of dogs with unstopped hemorrhage (starting at S). Time of administration is indicated at INJ.
Figure 12:
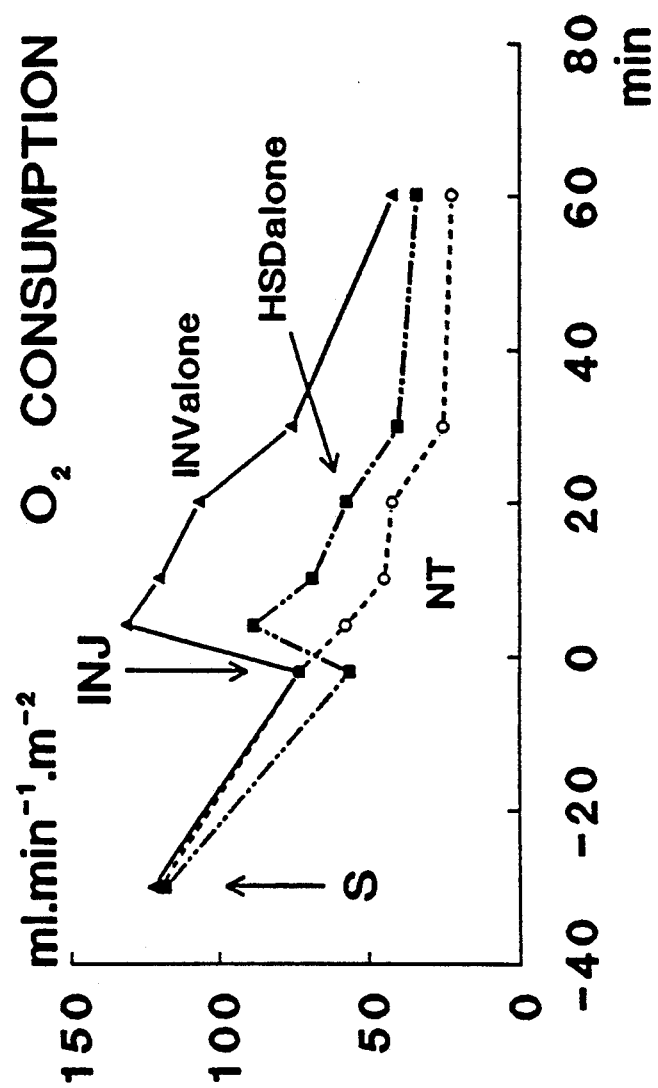
FIG. 12 shows the effect of NaCl/dextran (HSD) or NaCl/NaAc/dextran (INV) on $O_2$ consumption in dogs with unstopped hemorrhage (starting at S). Time of administration is indicated at INJ.

FIGS. 10–12 show that HSD alone and INV alone induce higher levels of arterial pressure, cardiac output and oxygen availability, in comparison with the NT group, but that INV alone induces the larger and longer lasting recovery of oxygen consumption.

These data show that the effects observed in the dog models of Example 2 regarding oxygen consumption are a consequence of the new formulation with sodium chloride:sodium acetate in the specified range.

EXAMPLE 4

The present example presents an expected useful application contemplated by the Applicants in treating hypovolemic shock in an animal.

A horse is suffering from colic and undergoes severe hypovolemic shock. The horse, weighing 1000 lbs, is immediately hooked up for intravenous infusion of a hypertonic solution of 2400 total osmolarity, 1 osmolal part sodium chloride and 7 osmolal parts sodium acetate. Administration is over a period of 10 min or less for a total infusion of 2.7 liters. The horse survives.

In a comparison, a horse weighing 1000 lbs is undergoing severe hypovolemic shock resulting from colic. A catheter is placed into a neck vein and a total of 30 liters of isotonic saline administered over a period up to one hour or longer. The horse dies while receiving treatment.

EXAMPLE 5

The present example outlines the procedure contemplated by the Applicants to be useful for intraoperative use.

A patient is at risk of hypovolemia due to surgical blood loss during an esophagectomy. When clinical signs of hypovolemia are observed, an infusion is begun with 250 ml of a solution containing 2 osmolar parts of sodium chloride and 6 osmolar parts of sodium acetate, total osmolarity of 1000. The solution is administered intravenously. Improved blood flow to organs and tissues is observed, without large increases in arterial pressure. There is no indication of increased bleeding due to higher arterial pressure.

The present invention has been described in terms of particular embodiments found by the inventors to comprise preferred modes of practice of the invention. It will be appreciated by those of skill in the art that in light of the present disclosure numerous modifications and changes can be made in the particular embodiments exemplified without departing from the intended scope of the invention. For example, additional components added to the sodium chloride/sodium acetate solution may be used to modify properties of the fluid for special applications. Other crystalloids such as salts with buffering capacity, cations such as potassium or magnesium, antishock drugs and the like may be included. These and obvious related modifications are contemplated to be within the scope of the claims.

REFERENCES

The references listed below are incorporated herein by reference to the extent that they supplement, explain, provide a background for or teach methodology, techniques and/or compositions employed herein.

1. Cone, J. B., Wallace, B. H., Caldwell, F. T., Jr., Smith, S. D. and Searcey, R., Am. J. Surg. 154, 585-588 (1987).
2. Fox, C. L., Jr., U.S. Pat. No. 3,993,750, Nov. 23, 1976.
3. Kramer, G. C. and Perron, P. R., U.S. Pat. No. 4,927,806, May 22, 1990.
4. Kramer, G. C., Perron, P., Lindsey, D. C., Ho, H. S., Gunther, R. A., Boyle, W. A. and Holcroft, J. W., Surgery 100, 239-246 (1986).
5. Kramer, G. C. and Holcroft, J. W., U.S. Pat. No. 4,908,350, Mar. 13, 1990.
6. Rocha e Silva, M., Velasco, I. T., Silia, R. R. et al., Am. J. Physiol. 253H 751 (1987).
7. Velasco, I. T., Oliveira, M. A., Oliveira, M. A., Rocha e Silva, M. Circ. Shock 21, 338-343 (1987).

What is claimed is:

1. A hypertonic composition for administration to an individual in need of isochloremic fluid resuscitation consisting essentially of about 2 molar parts of sodium chloride and about 6 molar parts of sodium acetate in a solution having a total osmolarity of at least 500 mOsm wherein said composition provides resuscitation which is substantially isochloremic and induces an initial increase in cardiac output.

2. The hypertonic pharmaceutical composition of claim 1 characterized as initiating an increase in tissue oxygen consumption.

3. The hypertonic pharmaceutical composition of claim 1 further comprising a biologically compatible metal salt.

4. The hypertonic pharmaceutical composition of claim 1 further comprising an amino acid.

5. The hypertonic pharmaceutical composition of claim 3 wherein the metal salt is a potassium, iron, magnesium or zinc salt.

6. The hypertonic pharmaceutical composition of claim 1 wherein sodium chloride to sodium acetate ratio is 2:6 with a total osmolarity of about 2400 mOsm/L.

7. A hypertonic pharmaceutical composition consisting essentially of 2 molar parts of sodium chloride, 6 molar parts of sodium acetate and a colloid selected from a group consisting essentially of dextrans, soluble starches, gelatins and colloids wherein said composition when administered to a patient in need of fluid resuscitation provides normalization of circulatory function including increased oxygen consumption and a rise in arterial blood pressure which is sufficient for maintaining blood perfusion to body organs and tissues in a recumbent recipient while avoiding excessive pressure rise.

8. The hypertonic pharmaceutical composition of claim 7 wherein the soluble starches are hydroxyethyl starches.

9. The hypertonic pharmaceutical composition of claim 7 further comprising a sugar.

10. A method of providing intravascular fluid support to a patient in need of fluid support, comprising administration to said patient of a bolus of a therapeutically effective amount of a pharmaceutical composition in accordance with claim 1.

11. The method of claim 10 wherein the patient is in circulatory shock or at risk for circulatory shock.

12. The method of claim 11 wherein the circulatory shock is from burn, hemorrhage, sepsis, allergic reaction or heart failure.

13. The method of claim 10 wherein administration is by intravascular infusion.

14. The method of claim 13 wherein administration is by rapid bolus infusion of about 4-6 ml/kg.

15. The method of claim 14 wherein the infusion is administered over a period of between 2 and 10 minutes.

16. The method of claim 10 wherein the total osmolar concentration is about 2400 mOsm.

17. The method of claim 10 wherein a patient in hypovolemic shock is administered a 2400 mOsm/L pharmaceutical composition in an amount of 4-6 ml/kg.

18. The method of claim 10 wherein a patient at risk of hemorrhage is administered a 1000 mOsm/L pharmaceutical composition in an amount of 4-6 ml/kg.

19. The method of claim 10 wherein a patient suffering from severe hypovolemia is administered near saturated solution in an amount of 1-2 ml/kg.

* * * * *

UNITED STATES PATENT AND TRADEMARK OFFICE
CERTIFICATE OF CORRECTION

PATENT NO. : 5,248,507
DATED : September 28, 1993
INVENTOR(S) : Mauricio R. e Silva, et al It is certified that error appears in the above-indentified patent and that said Letters Patent is hereby corrected as shown below:

Column 10, line 46, insert the word "a" after the word administered.

Signed and Sealed this

Twenty-ninth Day of March, 1994

Attest:

BRUCE LEHMAN

*Attesting Officer*  *Commissioner of Patents and Trademarks*